(12) United States Patent
Li et al.

(10) Patent No.: US 6,893,660 B2
(45) Date of Patent: May 17, 2005

(54) STABLE PHARMACEUTICAL COMPOSITIONS WITHOUT A STABILIZER

(75) Inventors: Boyong Li, Davie, FL (US); Xiu Xiu Cheng, Weston, FL (US)

(73) Assignee: Andrx Pharmaceuticals, Inc., Davie, FL (US)

( * ) Notice: Subject to any disclaimer, the term of this patent is extended or adjusted under 35 U.S.C. 154(b) by 31 days.

(21) Appl. No.: 10/301,474

(22) Filed: Nov. 21, 2002

(65) Prior Publication Data

US 2004/0101556 A1 May 27, 2004

(51) Int. Cl.$^7$ ............................. A61K 9/14; A61K 9/20
(52) U.S. Cl. ....................... 424/464; 424/465; 424/489; 514/970; 514/772.3; 514/781; 514/777; 514/770
(58) Field of Search ................................ 424/464, 465, 424/489, 451, 452

(56) References Cited

U.S. PATENT DOCUMENTS

| | | |
|---|---|---|
| 2,011,587 A | 8/1935 | Miller |
| 2,987,445 A | 6/1961 | Levesque |
| 3,143,463 A | 8/1964 | Holm et al. |
| 3,146,169 A | 8/1964 | Stephenson et al. |
| 3,538,214 A | 11/1970 | Polli et al. |
| 3,773,920 A | 11/1973 | Nakamoto et al. |
| 3,819,706 A | 6/1974 | Mehta |
| 3,885,046 A | 5/1975 | Mehta |
| 3,930,032 A * | 12/1975 | Harris et al. .................. 426/97 |
| 4,016,880 A | 4/1977 | Theeuwes et al. |
| 4,060,598 A | 11/1977 | Groppenbacher et al. |
| 4,077,407 A | 3/1978 | Theeuwes et al. |
| 4,116,241 A | 9/1978 | Theeuwes et al. |
| 4,135,514 A | 1/1979 | Zaffaroni et al. |
| 4,173,626 A | 11/1979 | Dempski et al. |
| 4,256,108 A | 3/1981 | Theeuwes |
| 4,309,405 A | 1/1982 | Guley et al. |
| 4,327,725 A | 5/1982 | Cortese et al. |
| 4,393,078 A | 7/1983 | Peck |
| 4,435,449 A | 3/1984 | Stern |
| 4,438,138 A | 3/1984 | Stern |
| 4,439,194 A | 3/1984 | Harwood et al. |
| 4,507,323 A | 3/1985 | Stern |
| 4,519,801 A | 5/1985 | Edgren |
| 4,539,198 A | 9/1985 | Powell et al. |
| 4,557,925 A | 12/1985 | Lindahl et al. |
| 4,571,395 A | 2/1986 | Peck |
| 4,650,669 A * | 3/1987 | Alexander et al. ............. 424/44 |
| 4,687,660 A | 8/1987 | Baker et al. |
| 4,769,027 A | 9/1988 | Baker et al. |
| 4,786,505 A | 11/1988 | Lovgren et al. |
| 4,798,826 A | 1/1989 | Peck |
| 4,853,230 A | 8/1989 | Lovgren et al. |
| 4,935,429 A | 6/1990 | Dackis et al. |
| 5,071,646 A | 12/1991 | Malkowska et al. |
| 5,098,715 A | 3/1992 | McCabe et al. |
| 5,358,970 A | 10/1994 | Ruff et al. |
| 5,427,798 A * | 6/1995 | Ludwig et al. ............. 424/464 |
| 5,472,708 A | 12/1995 | Chen |
| 5,503,846 A * | 4/1996 | Wehling et al. ............. 424/466 |
| 5,508,040 A | 4/1996 | Chen |
| 5,512,593 A | 4/1996 | Dante |
| 5,541,231 A | 7/1996 | Ruff et al. |
| 5,731,000 A | 3/1998 | Ruff et al. |
| 5,763,493 A | 6/1998 | Ruff et al. |
| 5,837,379 A | 11/1998 | Chen et al. |
| 5,968,553 A | 10/1999 | Maitra et al. |
| 5,990,175 A | 11/1999 | Pinsker |
| 6,033,686 A | 3/2000 | Seth |
| 6,096,341 A | 8/2000 | Seth |
| 6,110,973 A | 8/2000 | Young |
| 6,143,327 A | 11/2000 | Seth |
| 6,150,420 A | 11/2000 | Houdi et al. |
| 6,194,002 B1 | 2/2001 | Sherman |
| 6,197,827 B1 | 3/2001 | Cary |
| 6,210,716 B1 | 4/2001 | Chen et al. |
| 6,221,917 B1 | 4/2001 | Maitra et al. |
| 6,238,697 B1 | 5/2001 | Kumar et al. |
| 6,242,496 B1 | 6/2001 | Kulkarni et al. |
| 6,270,805 B1 | 8/2001 | Chen et al. |
| 6,277,887 B1 | 8/2001 | Young |
| 6,280,763 B1 | 8/2001 | Midha et al. |
| 6,306,436 B1 | 10/2001 | Chungi et al. |
| 6,312,716 B1 | 11/2001 | Midha et al. |
| 6,333,332 B1 | 12/2001 | Han et al. |
| 6,337,328 B1 | 1/2002 | Fang et al. |
| 6,342,496 B1 | 1/2002 | Jerussi et al. |
| 6,396,113 B1 | 5/2002 | Young |

FOREIGN PATENT DOCUMENTS

| WO | WO 00/30685 | 6/2000 |
|---|---|---|

OTHER PUBLICATIONS

Physicians' Desk Reference 46th Edition 1992 pg. 821 "Wellbutrin".

Cooper et al., Journal of Pharmaceutical Sciences, vol. 73, No. 8 Aug. 1984; "Determination of Bupropion and Its Major Basic Metabolites in Plasma by Liquid Chromatography with Dual-Wave Ultraviolet Detection" pp. 1104–1107.

Butz et al., The Journal of Pharmacology and Experimental Therapeutics, vol. 217, No. 31981; "Radioimmunoassay and Pharmacokinetic Profile of Bupropion in the Dog" pp. 602–601.

\* cited by examiner

*Primary Examiner*—James M. Spear
(74) *Attorney, Agent, or Firm*—Hedman & Costigan, P.C.

(57) ABSTRACT

Stabilized controlled release pharmaceutical preparations are disclosed in which active ingredient degradation is prevented without the use of a stabilizer. The active ingredient is sealed away from excipients that can adversely affect stability by sealing the excipients rather than the active ingredient. The preparations are substantially unaffected by exposure to storage conditions of elevated temperature and/or elevated relative humidity.

5 Claims, No Drawings

STABLE PHARMACEUTICAL COMPOSITIONS WITHOUT A STABILIZER

FIELD OF THE INVENTION

The present invention relates to novel, stable oral controlled-release dosage formulations without the need for acid stabilizers. More specifically, the present invention relates to highly stable solid oral dosage formulations in the form of a tablet or pellets that maintain at least 90% of initial drug or other active ingredients potency after one year.

BACKGROUND OF THE INVENTION

Stability is an important aspect of all forms of controlled release dosage forms and other formulations for active ingredients. Stability study requirements are covered in the *United States Pharmacopia* 24$^{th}$ Edition (USP XXIV), in the Good Manufacturing Practices (GMP) as well as in FDA Guidelines. The ingredients used in controlled release dosage forms often present special problems with regard to their physical stability during storage. Strategies used in the prior art to stabilize controlled release formulations include: insuring the individual ingredients are in a stable form prior to their incorporation into the product; retarding the instability by adding additional ingredients; inducing the individual ingredients to reach a stable state before the product is completed; changing the porosity and/or hydration level of a polymeric film to adjust the moisture content of the product; and proper packaging of the product.

In some instances, active ingredients of solid controlled release formulation degrade by hydrolysis. For example, hydrolysis of bupropion hydrochloride is encouraged in environments where the pH is above 4, as well as in the presence of (hydrophilic) excipients. The prior art shows that hydrolysis of certain active ingredients can be retarded in an acidic environment. Accordingly, acidified additives or formulations have been used to retard degradation.

Examples of prior art formulations of the drug bupropion hydrochloride demonstrate the use of acidic stabilizing ingredient to prevent degradation of the active ingredient. Bupropion hydrochloride is an aminoketone-derivative designated as (±)-1-(3-chlorophenyl)-2-[(1,1-dimethylethyl) amino]-1-propanone hydrochloride and described in U.S. Pat. Nos. 5,358,970; 5,427,798; 5,731,000, 5,763,493; Re. 33,994; 3,819,706 and U.S. Pat. No. 3,885,046. It is marketed as an antidepressant and as an aid to smoking cessation. The drug is chemically unrelated to tricyclic, tetracyclic or selective serotonin-reuptake inhibitors. Noradrenergic pathways and/or dopaminergic effects appear to be the primary mechanism for antidepressant and smoking cessation actions. The dosing regimen for sustained-release bupropion is once or twice daily.

The stability of bupropion hydrochloride and other active ingredients may be affected by factors including formulation and storage conditions. Heat lability of bupropion hydrochloride formulations is known. Although bupropion hydrochloride is stable in bulk and in most simple blends, the drug is unstable in complex mixtures such as granulations or tablets.

Stability studies of mixtures with lubricants show that bupropion is stable in the presence of talc but stability is poor in the presence of magnesium stearate or stearic acid. A lubricant, such as, magnesium stearate is often added to prevent picking and sticking on a high-speed rotary press. Bupropion formulations without stabilizers lose more than 50% of active ingredient potency at six weeks of accelerated conditions.

Labeling of conventional tablets or extended-release tablets of bupropion hydrochloride indicates storage at a temperature of 15–25° C. and protection from light and moisture. Extended release tablets of bupropion should be stored in tight, light-resistant containers at a temperature of 20–25° C. (USP Pharmacopeial Forum, Vol. 26(4): July–August 2000).

The prior art describes the use of stabilizers to prevent degradation of the active ingredient. For example, the patents summarized below teach the addition of an organic or inorganic acid as a separate stabilizing ingredient for formulations of bupropion hydrochloride.

Sustained release tablet forms of bupropion are described in U.S. Pat. No. 5,427,798, comprising a sustained release tablet where controlled release is achieved by combining bupropion particles with microcrystalline cellulose and hydrogel-forming high molecular weight, high viscosity grades of hydroxypropyl methylcellulose. Stabilization of this formulation is taught by addition of cysteine hydrochloride or glycine hydrochloride.

Stabilization by acidification of the environment in which degradation occurs in pharmaceutical compositions containing bupropion is disclosed in U.S. Pat. No. 5,968,553. In this patent, the stabilizer is an inorganic acid having an aqueous solution pH of about 0.5 to 4.0 at a concentration of about 0.31% w/w. The inorganic acids are selected from the group consisting of hydrochloric acid, phosphoric acid, nitric acid, and sulfuric acid. The stabilizer constitutes from about 0.01% to about 5% of the amount of bupropion hydrochloride in the composition.

Solid bupropion formulations containing acidic stabilizers are also disclosed in U.S. Pat. No. 5,358,970 where the stabilizer has an aqueous pH of about 0.9 to 4.0 at an aqueous solution concentration of about 6% w/w and are solid or liquid at 30° C. Stabilizers used are selected from the group consisting of L-cysteine hydrochloride, glycine hydrochloride, ascorbic acid, malic acid, sodium metabisulfite, isoascorbic acid, citric acid, tartaric acid, L-cysteine dihydrochloride or their combinations.

Stabilization of the commercially available Wellbutrin® SR is achieved by acidification with L-cysteine hydrochloride.

Although the prior art teaches incorporating acidification additives to reduce the hydrolytic degradation of active ingredients, it is less desirable because: 1) it may not be suitable for pharmaceutical compositions with basic excipients and 2) it represents additional ingredients in the formulation. The need exists for a stable controlled release bupropion formulation that does not require a stabilizer and which may be used with basic excipients. Such delayed delivery dosage formulations have a practical application, and represent a valuable contribution to the medical arts. The present invention provides such compositions, and offers efficient and cost effective methods of preparation.

SUMMARY OF THE INVENTION

The present invention meets the unfulfilled needs of the pharmaceutical industry by providing a stable oral dosage formulation that overcomes the problems of the prior art. The present invention may also have application to other solid delivery forms of active ingredients, such as algicides, antioxidants, air purifiers, biocides, bactericides, catalysts, chemical reactants, disinfectants, fungicides, fermentation agents, fertility inhibitors, fertility promoters, germicides, herbicides, insecticides, microorganism attenuators, pesticides, plant growth promoters, plant growth inhibitors, preservatives, rodenticides, sterilization agents, sex sterilants, and the like.

Accordingly, it is an object of this invention to provide a novel and useful sustained-release formulation that is free of any organic or inorganic acid stabilizing additive component. This represents an unexpected improvement in the art and substantially overcomes the disadvantages known to the prior art.

It is an object of the present invention to provide a formulation for solid delivery forms of other active ingredients.

It is also an object of the present invention to provide both a method of stabilizing bupropion hydrochloride to slow the degradation thereof and provide products that can be stored for long periods of time at room temperature, i.e., under humidity and temperature conditions usually encountered in pharmacies and medicine cabinets. It is a further object to provide solid oral dosage forms where the amount of active drug will be prevented from being reduced to less than about 90% of its labeled strength, and more preferably not less than about 95% of the labeled strength after one year of storage under the aforementioned usually encountered conditions.

It is also an object of the invention to provide an acid free, sustained-release bupropion dosage system that is therapeutically or biologically equivalent to sustained-release bupropion formulations that contain an organic or inorganic acid.

It is an object of the invention to produce a stable formulation of bupropion hydrochloride suitable for once daily administration, in the form of a blend of beads or pellets as a tablet or capsule dosage form that overcomes the need to add stabilizers.

Other objects, features and advantages of the invention are not taught in the prior art but will be more apparent to those versed in the art from the following specification, taken in conjunction with the accompanying claims.

DETAILED DESCRIPTION OF THE PREFERRED EMBODIMENTS

The invention provides sustained-release formulations that can provide an alternative to the prior art formulations. The prior art formulations typically require the presence of a stabilizer, such as an organic or inorganic acid. An embodiment of the subject invention provides for a stable bupropion hydrochloride formulation for once or twice daily dosing without the need for adding the acid or other stabilizing component.

Unlike the prior art, the subject invention favorably influences stability by physically sealing the excipients rather than chemically adjusting pH. In this novel formulation, stability is achieved, even in higher pH environments, by sealing the excipients rather than sealing the active drug, as has been previously done. This protective coating thereby prevents the absorption of moisture by the excipients during storage. Thus, the invention can be applied to any drug or other active component that will undergo hydrolytic decomposition in the presence of moisture and/or other moisture triggered decomposition reactions or other destabilization mechanisms.

Stabilizer, as the term is used herein, refers to compounds capable of chemically inhibiting or preventing degradation of bupropion hydrochloride. Stabilizers in prior art formulations were added to formulations of bupropion hydrochloride to improve chemical and physical stability. According to previous bupropion formulations containing stabilizers, tablets should retain about 80–90% or more of active ingredient at the end of one year in the presence of stabilizers.

The stability of bupropion hydrochloride formulated according to the present invention, without stabilizers, was tested in accordance with and exceeded current pharmaceutical industry standards for storage (i.e., four to twelve weeks at about 40° C. and about 75% relative humidity). Formulations of the present invention stored under these conditions retain at least about 90% of the bupropion hydrochloride present in the composition at the time of storage. In many instances, formulations of the present invention retain more than about 95% of their original potency, and more preferably retain at least about 98% of bupropion hydrochloride present in the composition at the time of storage. Standard procedures such as HPLC or UV spectroscopic methods may be used to determine the amount of active ingredient remaining after storage. Shelf life assay limits of 90 to 110 percent of the labeled strength tablet are applied. The design of the stability studies was in compliance with the general requirements suggested by the FDA stability guidelines.

The total amount of inactive ingredients in the formulations is preferably 30% or more of the weight of the bupropion.

Pharmaceutical compositions of the present invention generally contain from about 50 to about 300 mg of bupropion hydrochloride as the active ingredient. More preferably, compositions of the invention contain about 100 mg to about 200 of active ingredient and may be in the form of tablets, caplets or capsules.

Pharmaceutical compositions of the present invention as in Example 1 below, may contain combinations of low and high molecular weight osmopolymers. Osmopolymers are swellable, hydrophilic polymers that interact with water and aqueous biological fluids causing the osmopolymer to swell or expand and retain water in the polymer structure. One preferred group of osmopolymers are the polyethylene oxides. The preferred polyethylene oxides are those with higher molecular weight, i.e., $2 \times 10^6$ and higher, that provide delayed drug release via the hydrophilic polymer matrix. The drug release proceeds as a controlled diffusion, dependent on the molecular weight (hereinafter "MW") of the polyethylene oxide (PEO); the higher the MW, the slower the rate of drug released. A preferred PEO is Poly-ox WSR Coagulant (MW 5,000,000, viscosity 5,500–7,500 mPa·s at 25° C.).

The addition of an osmagent may enhance the regulation of the rate of diffusion through the membrane and thus enhance regulation of the rate of drug release. Preferred water-soluble resins for use as osmagents are those with MWs less than $0.6 \times 10^6$. Most preferred is Poly-ox WSR N-80 (MW 200,000) (viscosity of 65 to 115 mPa·s at 25° C.). When the drug is formulated by combining the higher MW polyethylene oxides (viscosity of 5000 to 20,00 mPa·s at 25° C.) with low MW polyethylene oxides (viscosity of 50 to 200 mPa·s at 25° C.), the release is controlled by the swelling of the polymer as well as by polymer erosion, thereby producing a substantially constant rate of delivery over a 24 hour period. A preferred concentration of the high MW to low MW polyethylene oxides for bupropion was determined to be a mixture of about 1:1.24 (wt./wt.) although other ratios are within the contemplated scope of the present invention.

The present invention discloses stabilization of the controlled release dosage form without the need for chemical stabilizers by sealing the low and high molecular weight polyethylene oxides with a water-soluble polymer, thereby physically separating them away from the bupropion. Any of the known film forming water-soluble polymers may be used in this regard. For example, water-soluble polymers such as hydroxypropylcellulose (HPC) and hydroxypropyl methylcellulose (HPMC) may be used as seal coats for the polyethylene oxides in this application. Generally, the HPC and HPMC useful as seal coats in the practice of the present invention have average molecular weights of 80,000 to 1,150,000, and 12,600 to 104,000, respectively. Preferred is hydroxypropylcellulose as in Examples 1.

Also, an effective amount of any generally accepted pharmaceutical lubricant may be added to compress the tablet cores of Example 1. Tablet lubricants are preferably selected from the group consisting of glyceryl monostearates, magnesium stearate, calcium stearate or stearic acid. Most preferably, magnesium stearate is present as a lubricant to prevent the tablets from sticking during processing on a high-speed rotary press. Magnesium stearate is added to the granulation to assist compression. In the preferred embodiment in Example 1 below, the magnesium stearate is used in an amount of less than about 1% by weight of the tablet, although other amounts known to those skilled in the art may be employed.

A glidant or anti-caking agent also may be employed in the practice of the present invention. Suitably, these may be chosen from any known such agents, such as, for example, colloidal silicon dioxide or talc. In Example 1 below, colloidal silicon dioxide is the preferred glidant.

Lactose may also be added as a tabletting filler, or diluent, which can aid in the processing and tableting. The use of lactose can be seen in Example 1. Preferably, anhydrous lactose may be used as a diluent. In a preferred embodiment, the optimal amount of lactose is found to be from about 25% to about 40% by weight of the formulation. Other such excipients known to those skilled in the art, such as sucrose, dextrose, lactose, microcrystalline cellulose, xylitol, fructose, sorbitol, and mixtures thereof also may be used.

The following examples illustrate the present invention and are not intended to limit the scope of the present invention.

EXAMPLE 1

The formulation contained the following ingredients in the following amounts:

|  | Weight (mg)/Tablet | % (Wt.) |
|---|---|---|
| Bupropion hydrochloride | 150.0 | 49.83 |
| Polyethylene Oxide (M.W. 200,000) | 59.4 | 19.93 |
| Polyethylene oxide (M.W. 5,000,000) | 47.7 | 15.95 |
| Hydroxypropylcellulose | 12.8 | 4.32 |
| Lactose Anhydrous | 27.7 | 9.30 |
| Colloidal Silicon Dioxide | 1.5 | 0.50 |
| Magnesium stearate | 0.9 | 0.30 |
| TOTAL | 300.0 | 100.13 |

In a GPGC-5 Glatt fluid-bed processor 2.477 kg of polyethylene oxide (M.W. 200,000) and 1.99 kg of polyethylene oxide (M.W. 5,000,000) were loaded. A solution of hydroxypropyl cellulose (0.532 kg) in acetone and isopropyl alcohol (2:1) was sprayed on the powders using the following settings:

| Inlet air temperature | 26–28° C. |
|---|---|
| Air volume | 450–480 m³/h |
| Outlet air regulation flap | 50 |
| Shaker interval | 2 seconds every 22 seconds |
| Pump rate | 30–70 mL/min |
| Atomization pressure | 2.5 bar |

After all the solution was sprayed, the granules were dried in the fluid-bed processor until the loss on drying (LOD) reached below 1%. The granules were unloaded from the fluid-bed processor and passed through a 20 mesh screen.

The bupropion hydrochloride, lactose, colloidal silicon dioxide were weighed out and sifted through a 30 mesh screen. The sifted ingredients were then blended with polyethylene oxide granules for 15 minutes. After mixing with magnesium stearate (sifted through a 30 mesh screen) for 5 minutes, the blend was compressed into tablets using 11/32" round, standard concave tooling.

Product stability data were obtained for this formulation stored for 5 months under accelerated conditions (40° C. and 75% relative humidity). The tablets retained 99.5% potency after 5 months of storage at 40° C. and 75% relative humidity.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof that do not depart from the spirit and scope of the invention.

The above-referenced patents and publications are hereby incorporated by reference.

What is claimed is:

1. A method for stabilizing pharmaceutical preparations in solid dosage forms by:

preventing direct contact between excipients that have a negative effect on stability of pharmaceutically active ingredients, said method comprising:

a) adding a sealing component to said excipients to form a sealed excipient component; and
b) combining said sealed excipient component with a composition comprising pharmaceutically active components to form a stable composition, wherein the sealed excipients comprise a combination of low molecular weight and high molecular weight polyethylene oxides.

2. The method of claim 1, wherein the sealed excipient ratio of high molecular weight to low molecular weight polyethylene oxides is 1:1.24 (wt./wt.).

3. A pharmaceutical composition in solid form comprising pharmaceutically active ingredients combined with excipients having a negative effect on stability, comprising:
(a) bupropion hydrochloride;
(b) a compressible tableting filler;
(c) a glidant;
(d) a lubricant; and
(e) a component comprising a mixture of:
   (i) a low molecular weight polyethylene oxide;
   (ii) a high molecular weight polyethylene oxide; and
   (iii) hydroxypropyl cellulose; as a sealing component to seal (i) and (ii).

4. A pharmaceutical composition of claim 3 comprising from about 50 to about 400 mg bupropion hydrochloride; from about 40 to about 80 mg polyethylene oxide (M.W. 200,000); from about 30 to about 70 mg polyethylene oxide (M.W. 5,000,000); from about 5 to about 20 mg hydroxypropylcellulose; from about 15 to about 40 mg lactose anhydrous; from about 0.5 to about 5 mg colloidal silicon dioxide and from about 0.25 to about 2.5 mg magnesium stearate.

5. A pharmaceutical composition of claim 4, comprising by weight, approximately,

| | | |
|---|---|---|
| bupropion hydrochloride | 150.0 mg | (49.83%) |
| polyethylene oxide (M.W. 200,000) | 59.4 mg | (19.93%) |
| polyethylene oxide (M.W. 5,000,000) | 47.7 mg | (15.95%) |
| hydroxypropylcellulose | 12.8 mg | (4.32%) |
| lactose anhydrous | 27.7 mg | (9.30%) |
| colloidal Silicon Dioxide | 1.5 mg | (0.50%) |
| magnesium stearate | 0.9 mg | (0.30%). |

* * * * *